(12) United States Patent
Ming

(10) Patent No.: US 10,420,595 B2
(45) Date of Patent: Sep. 24, 2019

(54) UNIVERSAL SELF-LOCKING ANATOMICAL PLATE FOR POSTERIOR OF ACETABULUM AND PELVIS

(71) Applicant: Li Ming, Ningbo (CN)

(72) Inventor: Li Ming, Ningbo (CN)

(*) Notice: Subject to any disclaimer, the term of this patent is extended or adjusted under 35 U.S.C. 154(b) by 972 days.

(21) Appl. No.: 14/925,706

(22) Filed: Oct. 28, 2015

(65) Prior Publication Data

US 2017/0086893 A1  Mar. 30, 2017

(30) Foreign Application Priority Data

Sep. 25, 2015 (CN) .......................... 2015 1 0620134

(51) Int. Cl.
*A61B 17/80* (2006.01)
*A61B 17/17* (2006.01)

(52) U.S. Cl.
CPC ...... *A61B 17/8066* (2013.01); *A61B 17/1728* (2013.01); *A61B 17/8057* (2013.01)

(58) Field of Classification Search
CPC . A61B 17/80; A61B 17/8052; A61B 17/8057; A61B 17/8061; A61B 17/8066; A61B 17/8071; A61B 17/8076; A61B 17/8085
USPC ................................................. 606/902–906
See application file for complete search history.

(56) References Cited

U.S. PATENT DOCUMENTS

| | | | |
|---|---|---|---|
| 6,283,969 B1 * | 9/2001 | Grusin | A61B 17/1728 606/280 |
| 8,449,581 B2 * | 5/2013 | Helfteren | A61B 17/8071 606/280 |

FOREIGN PATENT DOCUMENTS

| | | | |
|---|---|---|---|
| CN | 102204841 A | | 10/2011 |
| CN | 103393460 A | * | 11/2013 |
| CN | 105078559 B | | 6/2017 |
| FR | 2631539 A1 | * | 11/1989 ......... A61B 17/8066 |

OTHER PUBLICATIONS

Office Action of corresponding CN application, published on Jan. 3, 2017.

* cited by examiner

*Primary Examiner* — Si Ming Ku
(74) *Attorney, Agent, or Firm* — Wang Law Firm, Inc.

(57) ABSTRACT

A universal self-locking anatomical plate for posterior of acetabulum and pelvis, which includes a right plate (1), a plurality of screws (2) and a guiding sleeve (3). The right plate (1) includes a region-a, a region-b, a region-c, a region-d and a region-e, which can respectively fix a certain region of an acetabulum, the region-a is provided thereon with three first locking holes for receiving the locking screws, the region-b is provided thereon with at least two second locking holes, the region-c is provided thereon with two positioning holes and twelve third locking holes, the region-d is provided thereon with three fourth locking holes, and the region-e is provided thereon with one fifth locking hole. The plate has an optimized structure, and has three capabilities: good safety, good stability, and biomechanic matching. Additionally, the fitness of the plate to the surface of the acetabulum mode is good.

8 Claims, 12 Drawing Sheets

UNIVERSAL SELF-LOCKING ANATOMICAL PLATE FOR POSTERIOR OF ACETABULUM AND PELVIS

RELATE APPLICATIONS

This application is a patent application which claims the benefit of Chinese Invention Application 201510620134.8, filed on Sep. 25, 2015, the specification of which is incorporated herein by this reference.

FIELD OF THE INVENTION

The present invention relates to the technical field of instruments for treating acetabular fractures in orthopedic surgery, and in particular to a universal self-locking anatomical plate for posterior of acetabulum and pelvis, which is suitable for the treatment of the acetabular fracture, such as the fracture of the posterior of acetabulum (posterior column/posterior wall) and the fracture of the quadrilateral regions of acetabulum or acetabular dome, where an internal fixation should be plated into the patient in an approach from the posterior of acetabulum, and is also suitable for the case of bony defect of the posterior and inside of acetabulum in the hip replacement and revision surgery.

DESCRIPTION OF THE PRIOR ART

With the deepening of researches on the pelvic and acetabular biomechanics, the deepening of researches on the pelvic and acetabular fracture mechanism and the anatomical imaging, the progress of researches on metallic properties of built-in material and the continuous improvement of the open reduction and internal fixation technology, the surgical treatment of acetabular fracture is increasingly and widely accepted. Anatomical reduction and firm fixation are critical to treat displaced and unstable acetabular fracture. However, there are the following major problems.

(1) As the anatomical shape of acetabulum and pelvis is irregular, during the operation involved with the fracture of posterior wall/posterior column of acetabulum, it is required to employ improved Kocher-Langenbeck approach exposure. However, the position and shape of soft tissue structures, such as, sciatic nerves and blood vessel nerves in the superior gluteal, limit a range of exposure on an operative incision and thus limit the size and strength of an implant. As pelvic organs and important vessels are in the front interior of the hip joint, inappropriate screw placement is likely to cause accident injury or misplacement into the hip joint to damage a normal joint, thereby bringing a great difficulty and risk to the operative reduction and internal fixation.

(2) The fixation of the fracture of posterior of acetabulum includes bifurcated plates (also referred to as dovetail steel plates), elastic steel plates, locking compression steel plates, reconstruction steel plates, memory alloy, common screws or cannulated screws, steel wires, steel needles, etc. The complications caused by internal fixation by conventional steel plates include iatrogenic sciatic nerve injury, injury of superior gluteal artery and vein, femormal head injury, lost of postoperative fracture reduction, incursion of screws into joints and even slippage and breakage of screws, etc. A plate for posterior of acetabulum and pelvis, produced by a certain company in China, is actually a combination of two arc reconstruction steel plates and thus has no guiding sleeve structure for orienting the screw placement. As the screw placement is carried out only by the subjective experience of an operator, the locking screws are likely to intrude into a joint, thereby resulting in screw fixation failure and inefficient screw fixation. Consequently, the safety of screw placement during an operation cannot be ensured. The screws are likely to get into a joint by mistake or damage important vascular nerves and organ tissues surrounding the fracture to cause secondary damage. Such a plate shows low safety.

(3) For the comminuted fracture within a region of the posterior of acetabulum, there is no special internal fixation instrument. Some surgeons use reconstruction plates to fix fracture blocks. Although this is effective for a large and complete bone block, it is unable to fix free comminuted fracture blocks effectively. This method has the advantages of incomplete fracture reduction, bone loss and unstable fixation. As it is required to perform manual shaping during the operation according to the shape characters of the acetabulum of a patient, the fit of the plate shaped during the operation with the bone cannot be ensured. Meanwhile, due to prolonged time of operation, prolonged time of exposure of an incision, increased dose of anaesthetic, increased operation bleeding and the like, various potential operation risks and complications increase. The poor shaping of the plate and the non-fitting of the plate with the bone will cause loose and displacement at the fracture, and thus result in pain and stress shielding of the bone. As a result, the risk of poor fracture union or malunion is increased.

(4) For the specially comminuted fracture of the posterior of acetabulum, particularly the fracture in an external ⅓ region of the real of acetabulum, there is no special and effective internal fixation instrument in the world. At present, conventionally, reconstruction steel plates plus dovetail steel plates or elastic steel plates are used for fixation, where two to four plates are required. As a non-uniform shearing force and a slip displacement exist between the plates, the internal stress of an overall internal fixation system of the plates and screws is disordered, resulting in high potential risk of the loss of reduction after internal fixation. It fails to ensure early and safe functional training to restore functions of the joint. Consequently, the long in-bed time of the patient will cause postoperative synarthrophysis and partial lose of functions. The repeated shaping and bending of a plate will leave notches or scratches on the surface of the plate, so that the internal stress concentration points of the plate increase and the risk of fatigue breakage of an implant thus increases.

(5) As the fixation of lateral fracture of the posterior of acetabulum is very difficult and it is very likely to result in poor reduction and infirm fixation, the incidence of complications, such as nonunion/delayed union or malunion of acetabular fracture, traumatic arthritis, injury of important vascular nerves, breakage of implants, failed or inefficient fixation, operation failure and the like, is relatively high.

(6) For the compression fracture involved with a loading region of the acetabular dome, it is required to perform bone grafting and fixation. However, as there is no any effective internal fixation device at present and fixation is still carried out by reconstruction steel plates.

At present, the steel plates used internationally have the following problems: they are not inconformity with the biomechanical transmission system of pelvis and acetabulum (i.e., the mechanical conduction path of bone) and not fit with the surface morphology of acetabulum, thereby causing disordered transmission of the internal stress of bone and resulting in disadvantageous effects to fracture union. For the free comminuted fracture blocks of the posterior wall of acetabulum, two to four steel plates are required, and the expense of a patient increases. There is no internal fixation instrument suitable for the osteoporotic fracture of acetabulum and pelvis at present. With the deep going of "micro-invasive surgical treatment concept" in the modern orthopaedics, it is required to achieve the best clinical effect with the least possible operation wound.

In conclusion, the internal fixation of pelvis and acetabulum has high requirements to the implant material and mated operating instruments.

SUMMARY OF THE INVENTION

It is a technical problem to be solved by the present invention is to provide a plate which has an optimized structure, an easy usage, a good universality, a good fitness to the surface of the acetabulum mode, and has three capabilities: a good safety, a good stability, and matching with the biomechanics, not only suitable for the simple fracture of posterior wall of an articular surface of the acetabulum, but also suitable for all fractures in regions surrounding the articular surface of the acetabulum. The plate is designed according to the traveling direction of internal bone trabecula of the pelvis and acetabulum model.

For settling the technical problem, the universal self-locking anatomical plate for posterior of acetabulum and pelvis, comprising a right plate, a plurality of screws and a guiding sleeve for guiding drilling of the screws;

wherein the right plate has a central axis, a longitudinal section, an edge, and a central portion, the longitudinal section along the central axis of the right plate has a smooth arc surface, and the right plate vertically comprises a region-a, a region-b, a region-c, a region-d and a region-e, which can respectively fix a certain region of an acetabulum; the right plate comprises, on sideways, a region-A, a region-B, a region-C and a region-D; the region-a is provided thereon with three first locking holes for receiving the screws, the region-b is provided thereon with at least two second locking holes, the region-c is provided thereon with two positioning holes and twelve third locking holes, the region-d is provided thereon with three fourth locking holes, and the region-e is provided thereon with one fifth locking hole; and an angle between the axis of each screw and a line vertical to the surface of each corresponding locking hole is in range of 0°-20°; and each of the first locking holes, the second locking holes, the third locking holes, the fourth locking holes, the fifth locking hole has an internal thread.

While, the left plate is in an enantiomorphous configuration of the said right plate. That is, a plate with an enantiomorphous configuration of the said right plate is in the scope of the present invention.

Using the above technology, the plate of the present invention has three capabilities. The first capability is good safety, the direction of the locking holes all avoid the joint of the acetabulum, which ensure the screws not be screwed into the joint of the acetabulum and make the usage of the plate more safe. The second capability is good stability, each of region-a to region-e and each of region-A to region-D can fix a corresponding region of the acetabulum, after the screws screwed, it can satisfy for treating the fracture of the upper, the lower, the outer, the medial, the posterior, or the anterior of the acetabulum, anyone of these six parts of acetabulum. And in the operation, it only needs an incision at the posterior of the acetabulum to fix any parts of the acetabulum and the fracture of anyone of these six parts of the acetabulum can be treated, there is no need to open another incision at the anterior of the acetabulum as usual, therefore, the operation wood is reduced and a good stability is achieved. The third capability is matching with the biomechanics, as the right plate is design with transverse five region-a to region-e which are matching with the distribution direction of tension bone trabecula at the medial of the acetabulum and pelvis, and longitudinal four regions which are matching with the distribution direction of compression bone trabecula at the medial of the acetabulum and pelvis.

The plate of the present invention can be improved with the following technologies.

As a preference, a first connecting bridge and a second connecting bridge are extended outward from the region-a, the first connecting bridge defines a first connecting hole, the second connecting bridge defineds a second connecting hole; a third connecting bridge and a fourth connecting bridge are extended laterally away from the region-c, the third connecting bridge defines a third connecting hole, the fourth connecting bridge defines a fourth connecting hole.

As a preference, the first connecting hole and the second connecting hole each has a diameter of 4.5 mm, and a distance between centers of the first connecting hole and the second connecting hole is 36 mm; the third connecting hole and the fourth connecting hole each has a diameter of 3.5 mm, and a distance between centers of the third connecting hole and the fourth connecting hole is 20 mm.

As a preference, the first connecting bridge, the second connecting bridge, the third connecting bridge and the fourth connecting bridge each defines a groove, and each groove is respectively closer to the central axis of the right plate relative to the first connecting hole, the second connecting hole, the third connecting hole and the fourth connecting hole.

Preferably, each groove is 3-5 mm in length and 2.5 mm in width.

Preferably, two compensation holes are respectively provided at a joint between the third connecting bridge and the region-c, and a joint between the fourth connecting bridge and the region-c, the compensation holes are in communication with the adjacent grooves.

Preferably, a first annular gap is provided between the third locking holes on a rightmost edge of the region-c, and a second annular gap is also provided between the fourth locking hole on a rightmost edge of the region-d and the adjacent third locking hole.

Preferably, for positioning the locking holes, the right plate is defined with three longitude lines and eleven latitude lines; three first locking holes are located on a same first latitude line and respectively on the three longitude lines; at least two second locking holes are provided between the first latitude line and a third latitude line and located in turn on a first longitude line and a second longitude line; two, one, two, one, two, one and three third locking holes are respectively located on a third latitude line, a fourth latitude line, a fifth latitude line, a sixth latitude line, a seventh latitude line, an eighth latitude line and a ninth latitude line; three fourth locking holes are located on a same tenth latitude line and respectively on three longitude lines; the fifth locking hole is located on an eleventh latitude line and the second longitude line; and, a thickness of the edge of the plate is 50% to 70% of that of the central portion of the plate.

Preferably, one of the positioning holes is located between the fifth latitude line and the seventh latitude line, while the other positioning holes is located between the ninth latitude line and the tenth latitude line.

Preferably, front projections of the region-c and the region-d are in arc bending rightward, while left projections thereof are in arc bending outward; and, the right plate has a thickness ranging from 15.0 mm to 32.0 mm and a width ranging from 5.0 mm to 18.0 mm.

Compared with the prior art, the plate of the present invention is accordant with the shape of the posterior wall of the acetabulum and biomechanical characters, fully takes the convenience and safety of the surgical operation within a limited operative incision space into consideration, reduces the potential risk of damaging important vascular nerves and organ tissue models within the fracture region, is advantageous for the surgical operation, and reduces the operation wound, operation time, bleeding during the operation and the risk of operation damage. Meanwhile, the instrument provided by the present invention reduces the material and cost of implant and increases the fixation area of fragments surrounding the acetabulum.

After an implant is implanted into a bone model, there is a disadvantage that the stress is too much concentrated on screws at a fracture end. The present invention is in conformity with four principles of the orthopaedic biomechanical internal fixation, i.e., load sharing principle, neutral principle, principle of tension band and principle of compression band; the present invention is designed according to the traveling direction of internal bone trabecula of the pelvis and acetabulum model; and a connecting bridge structure is additionally provided. The stress is uniformly distributed on the screws at the fracture end, so that the loose and breakage of the screws are avoided, and the complications such as the loosing, displacement and pain of the implant at the later stage of the fracture and the stress shielding of bone are reduced. The instrument may bear the activity load of the hip joint model and the pelvis model like a normal bone, facilitate the union of fracture in an manner most advantageous for the patient, increase the success rate of the fracture internal fixation operation, improves the operation efficiency, reduce the complications related to fracture and help the recuperation of the patient soon.

Compared with the prior art, the present invention also has the following advantages:

(1) Two regions are provided on the plate, and the volume of a main body region is obviously smaller. By placing the plate in a smaller operative incision, the stripping damage to the soft tissue of the fracture wound is reduced, and the disturbance to the residual blood supply is also reduced.

(2) As the volume of the main body region is obviously smaller, the metal material to be implanted into the human body is reduced, the coverage area of the plate to the bone surface is reduced, the blood circulation at the fracture site is protected, and the fracture union is facilitated.

(3) By enhancing the fixation to the dome region of the acetabulum, the re-displacement of fracture blocks within the loading region on the dome of the acetabulum due to functional training is avoided, the normal mating and alignment of the articular surface of the acetabulum and a femoral head model is maintained, and the normal stable state of the hip joint is kept. The postoperative early activities of a patient are ensured; the complications such as bedsore, ruinary tract infection, hypostatic pneumonia, muscle atrophy of lower limbs, osteoporosis, reduction of digestive function, cardiopulmonary miopragia and deep venous thrombosis of lower limbs, caused by long-term sickbed, are reduced; and it is ensured that the patient may restore partial movements of the hip joint three days after the operation.

(4) A fixed passageway to the anterior column/anterior wall of the acetabulum is additionally provided on the plate. By fixing the fracture of the anterior column/anterior wall of the acetabulum from a posterior incision, one anterior fixed operative incision is omitted, a plate for fixing the fracture of the anterior column/anterior wall of the acetabulum is omitted, both of which greatly reduce the operative wound and the implant material and cost.

(5) By increasing fixed screw holes running from the bottom of the acetabulum to the ischial tubercleregion, the fixation to the ischial spine region is increased, and the deficiency, that the ischial spine region below the interior of the acetabulum cannot be effectively fixed, is overcome.

(6) By enhancing the fixation to the comminuted fracture of the ⅓ region below the external rim of the posterior wall of the cetabular model, the displacement and absorption of free fine fracture fragments are avoided, and the defect, that the ⅓ region below the posterior wall of the cetabular model cannot be effectively fixed, is overcome.

(7) For the attachment of the plate, a connecting bridge structure is provided. The connecting bridge structure is in conformity with the traveling direction of compression bone trabecula and tension bone trabecula inside the pelvis and acetabulum bone, meets the biomechanical requirements, and solves two drawbacks of breakage and failed fixation of screws of the implant.

(8) The outlets of the screws are all designed in a safe direction, so that the screws are prevented from puncturing neighboring important vascular nerve structures after penetrating through bone cortex.

DETAILED DESCRIPTION OF THE PREFERRED EMBODIMENT

To enable a further understanding of the innovative and technological content of the invention herein refer to the detailed description of the invention and the accompanying drawings below:

The reference numbers and the corresponding component names are listed as below:

1: right plate; 11: first connecting bridge; 11a: first connecting hole; 12: second connecting bridge; 12a: second connecting hole; 13: third connecting bridge; 13a: third connecting hole; 14: fourth connecting bridge; 14a: fourth connecting hole; 15: annular gap; 16: groove; 2: locking screw; 21: connector; 22: first external threads; 23: self-tapping groove; 3: guiding sleeve; 3a: guide hole; 31: working head; 32: second external threads; 33: handle; 33a: knurls; a: region-a; b: region-b; c: region-c; d: region-d; e: region-e; a1: first locking hole; b1: second locking hole; c1: third locking hole; c2: positioning hole; c3: compensation hole; d1: fourth locking hole; e1: fifth locking hole; J1: first longitude line; J2: second longitude line; J3: third longitude line; W1: first latitude line; W2: second latitude line; W3: third latitude line; W4: fourth latitude line; W5: fifth latitude line; W6: sixth latitude line; W7: seventh latitude line; W8: eighth latitude line; W9: ninth latitude line; W10: tenth latitude line; W11: eleventh latitude line; Z1: posterior superior iliac spine; Z2: greater sciatic notch; Z3: ischial spine; Z4: ischial tuberosity; Z5: inferior acetabular rim; Z6: superior acetabular rim; Z7: anterior inferior spine; Z8: anterior superior spine; Z9: iliac tuberosity; a: angle; L1: axis of a screw; L2: a line vertical to the surface of a locking hole.

FIG. 1-8 show a preferred embodiment of a universal self-locking anatomical plate for posterior of acetabulum and pelvis. The plate comprises a right plate 1, multiple locking screws 2, and a guiding sleeve 3 for guiding the drilling direction of the locking screws 2. The left plate is just in an enantiomorphous configuration of the right plate 1.

The right plate has a central axis, a longitudinal section, an edge, and a central portion. The longitudinal section of a central axis of the right plate 1 has a smooth arc surface.

The right plate 1 vertically (from top to bottom in turn) includes a region-a, a region-b, a region-c, a region-d and a region-e, which are all in arc and can respectively fix a certain region of an acetabulum.

Figure 12:
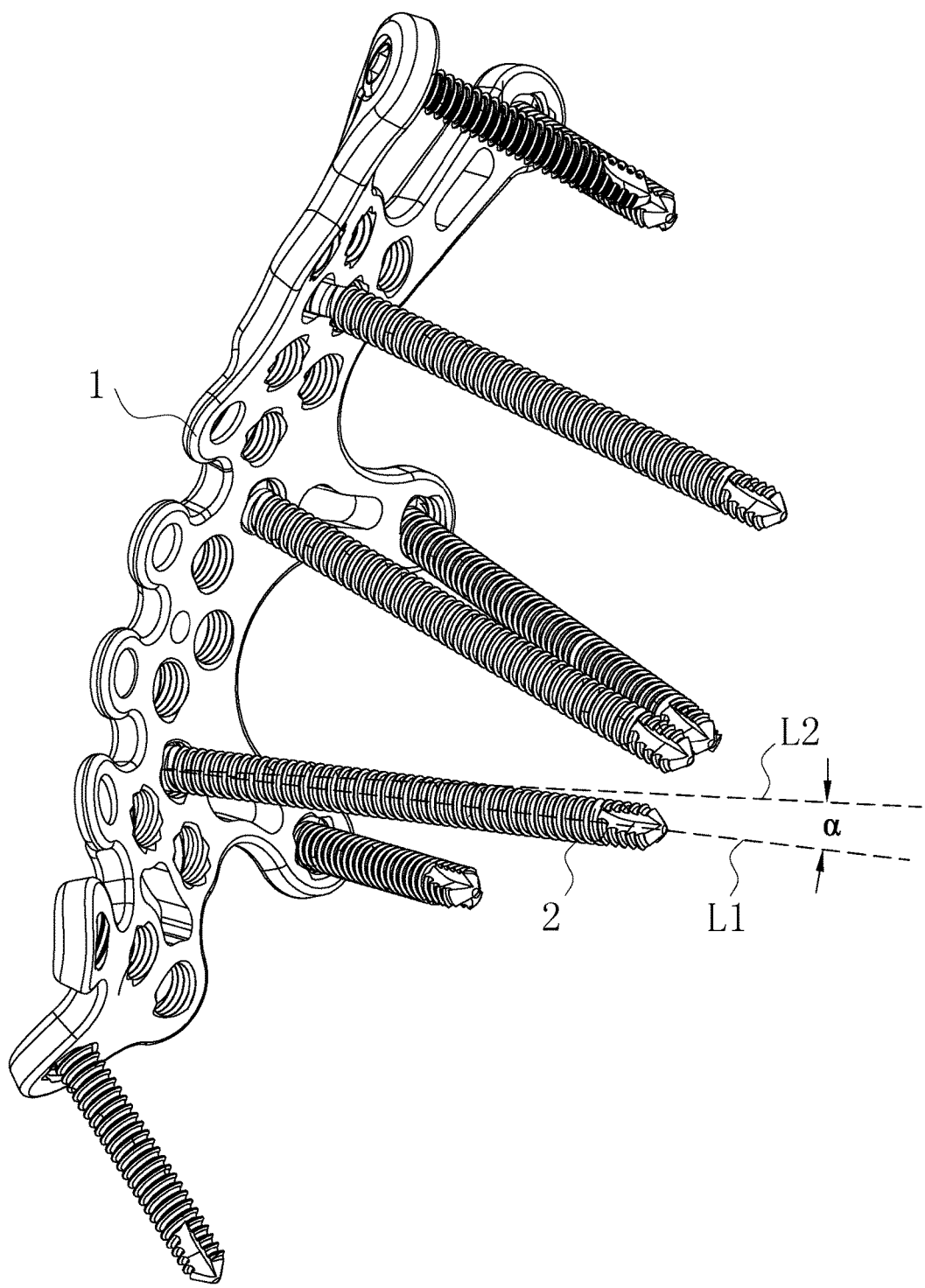
FIG. 12 is a perspective view of the plate with some locking screws according to the embodiment of the present invention showing the angle of each locking screw.

The region-a is provided thereon with three first locking holes a1 for receiving the locking screws 2, the region-b is provided thereon with at least two second locking holes b1, the region-c is provided thereon with two positioning holes c2 and twelve third locking holes c1, the region-d is provided thereon with three fourth locking holes d1, and the region-e is provided thereon with one fifth locking hole e1; and the angle α between the axis L1 of each screw 2 and a line L2 vertical to the surface of each corresponding locking hole is in range of 0°-20°, for example 5°, 10°, 15°, 20°. FIG. 12 illustrates an angle between the axis L1 of one locking screw 2 and a line L2 vertical to the surface of a corresponding locking hole. When in an actual operation, each angle α can be understood as the inserting direction of each locking screws 2 relative to the surface of plate 1 where the corresponding locking hole is, the operator will adjust each angle α of each locking screws 2 according to the actual situation, so that each locking screw 2 will not be screwed into a joint of acetabulum and pelvis or one important blood vessel or nerve system or other organs adjacent of the injured area to ensure them not be injured.

Each of the first locking holes a1, the second locking holes b1, the third locking holes c1, the fourth locking holes d1, the fifth locking hole e1 respectively has an internal thread on the inner wall thereof.

A connector 21 is provided on the top of each locking screw 2, and first external threads 22 capable of being in screw connection to the internal lockhole threads are formed on the periphery of the connector 21. A working head 31 is provided on the bottom of the guiding sleeve 3, and second external threads 32 capable of being in screw connection to the internal lockhole threads are formed on the periphery of the working head 31. A guide hole 3a is provided on the axis of the guiding sleeve 3.

A handle 33 is provided on the top of the guiding sleeve 3, and knurls 33a are provided on the periphery of the handle. The guiding sleeve 3 has a length of 120 mm to 200 mm, an inner diameter of 2.1 mm to 3.8 mm and an outer diameter of 4.2 mm to 9.0 mm.

A regular hexagonal or regular pentagonal cavity fitted with a mounting tool is provided at an upper part of the connector 21 of each locking screw 2, and the locking screw 2 has a diameter of 2.5 mm to 4.5 mm.

Of course, common screws or cannulated lag screws can be instead of the locking screws 2. Three self-tapping grooves 23 for allowing the locking screw 2 to be screwed therein are formed on the bottom of the locking screw 2. The tangent line of the self-tapping grooves 23 forms an included angle of 45° to 60° with the longitudinal axis of the locking screw 2. The arrangement of the self-tapping grooves 23 not only is convenient for the screwing-in of the locking screw 2, but also may reduce the puncturing effect to tissue and improve the holding force of the threads. The common screw is a universal 3.5 mm screw used for fracture internal fixation currently.

Figure 1:
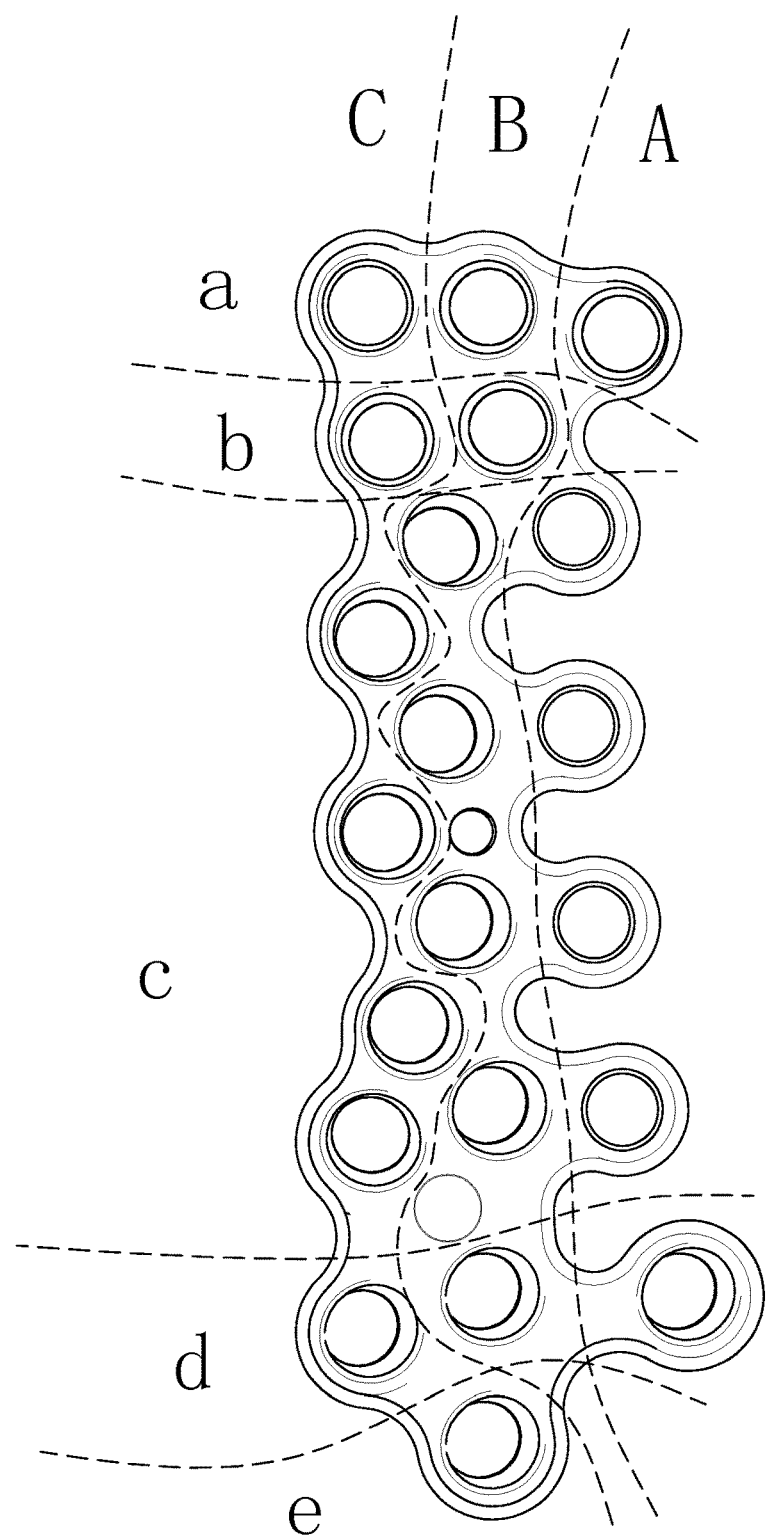
FIG. 1 is a perspective view of the plate according to an embodiment of the present invention showing five locking bocks (a-e).
Figure 2:
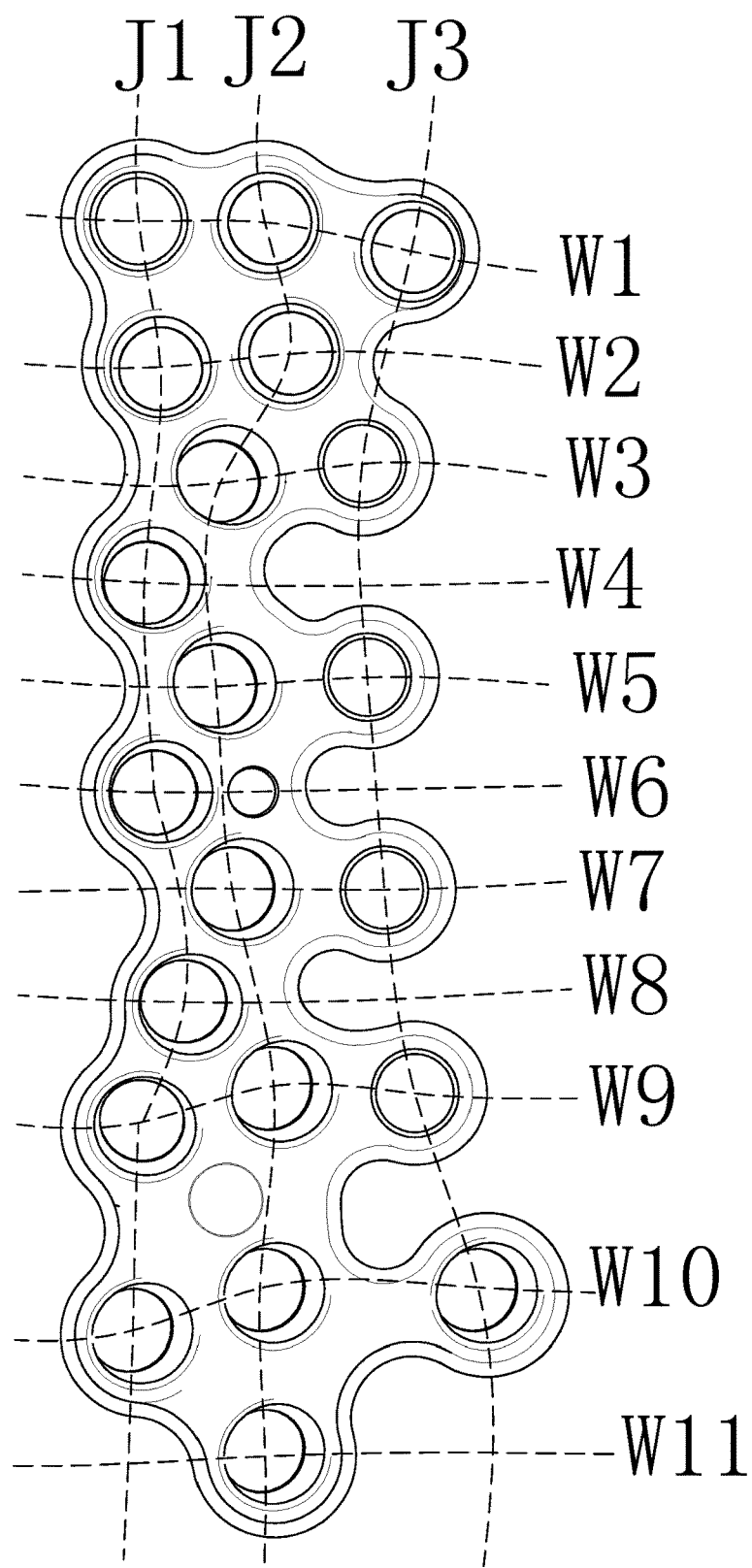
FIG. 2 is a perspective view of the plate according to the embodiment of the present invention showing all the locking holes on the five locking bocks.
Figure 3:
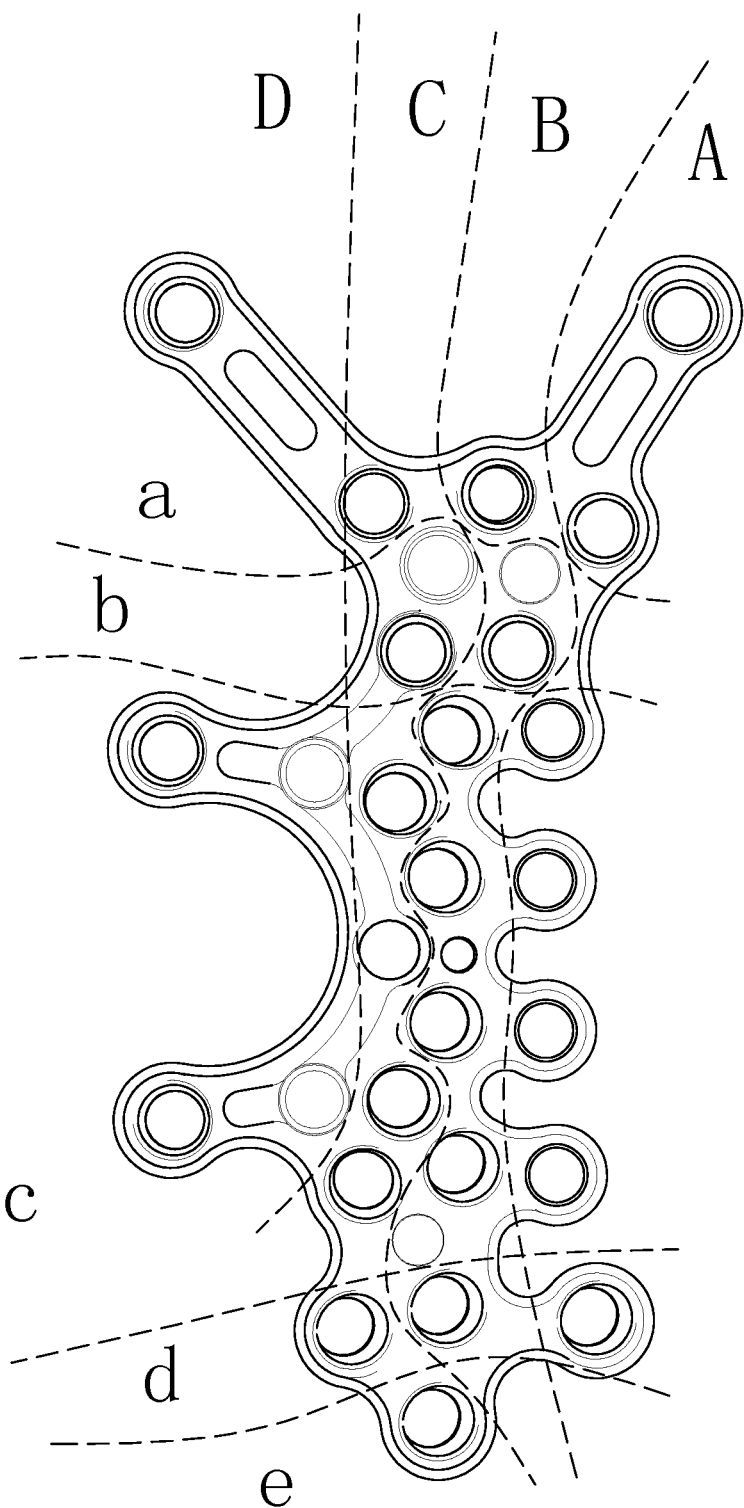
FIG. 3 is a perspective view of the plate according to the embodiment of the present invention showing five locking bocks (a-e) and region-A, region-B, region-C and region-D.

As shown in FIG. 3, a first connecting bridge 11 and a second connecting bridge 12 are extended outward respectively from two sides of the region-a, the first connecting bridge 11 has a first connecting hole 11a at the end thereof, the second connecting bridge 12 has a second connecting hole 12a at the end thereof;

a third connecting bridge 13 and a fourth connecting bridge 14 are laterally away from the region-c, the third connecting bridge 13 has a third connecting hole 13a at the end thereof, the fourth connecting bridge 14 has a fourth connecting hole 14a at the end thereof.

In this embodiment, each of the first connecting hole 11a and the second connecting hole 12a has a diameter of 4.5 mm, and a distance between the centers of the first connecting hole 11a and the second connecting hole 12a is 36 mm; each of the third connecting hole 13a and the fourth connecting hole 14a has a diameter of 3.5 mm, and a distance between the centers of the third connecting hole 13a and the fourth connecting hole 14a is 20 mm.

As shown in FIG. 3, the first connecting bridge 11, the second connecting bridge 12, the third connecting bridge 13 and the fourth connecting bridge 14 each defines a groove 16, and each grooves is respectively closer to the central axis of the right plate 1 relative to the first connecting hole 11a, the second connecting hole 12a, the third connecting hole 13a and the fourth connecting hole 14a.

In this embodiment, each grooves 16 is 5±3 mm in length and 2.5±1 mm in width.

In this embodiment, two compensation holes c3 are respectively provided at a joint between the third connecting bridge 13 and the region-c, and a joint between the fourth connecting bridge 14 and the region-c, the compensation holes c3 are in communication with the adjacent groove 16.

In this embodiment, a first annular gap 15 is provided between the third locking holes c1 on a rightmost edge of the region-c, and a second annular gap 15 is also provided between the fourth locking hole d1 on a rightmost edge of the region-d and the adjacent third locking hole c1.

Figure 4:
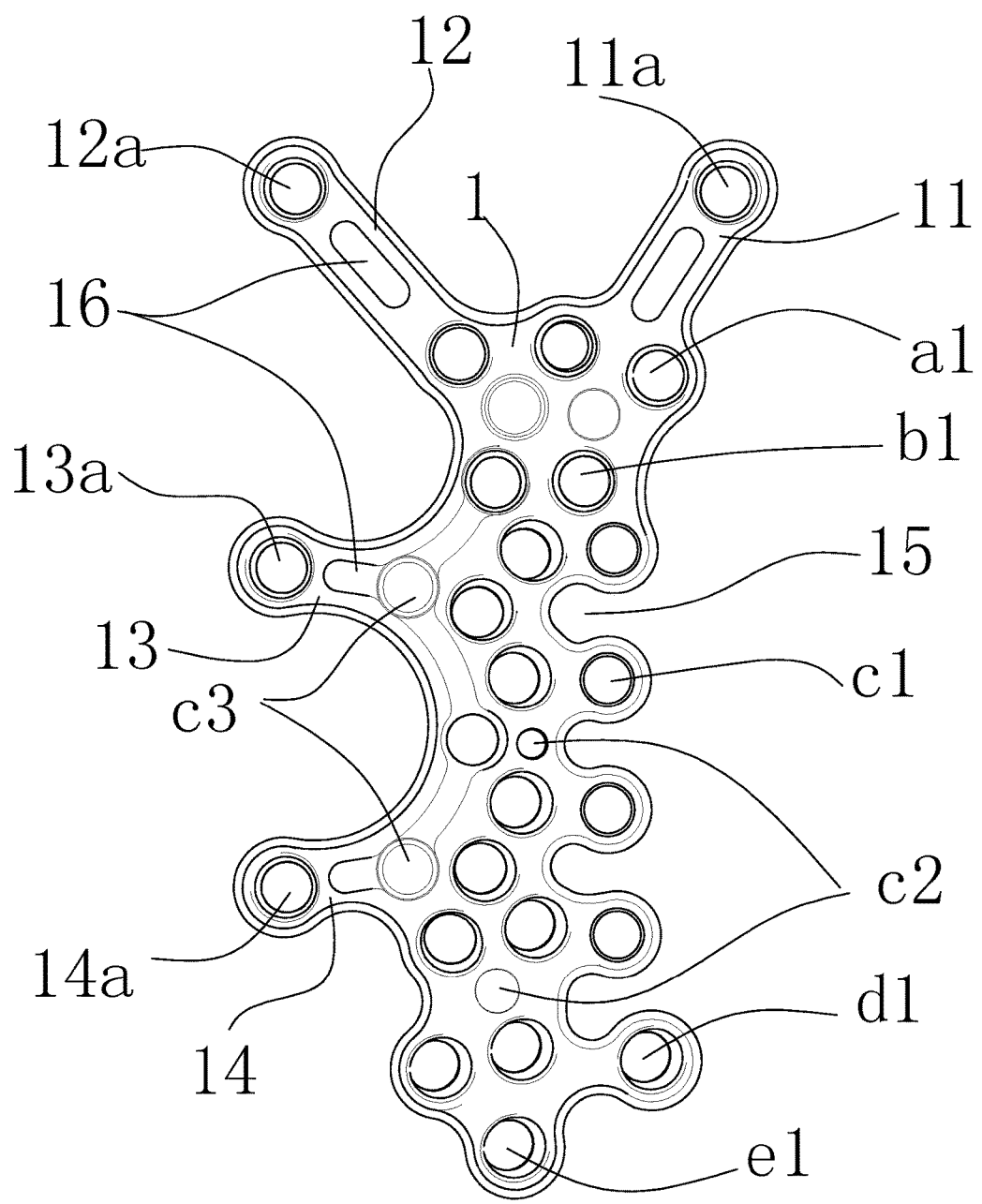
FIG. 4 is a front view of the plate according to the embodiment of the present invention.
Figure 5:
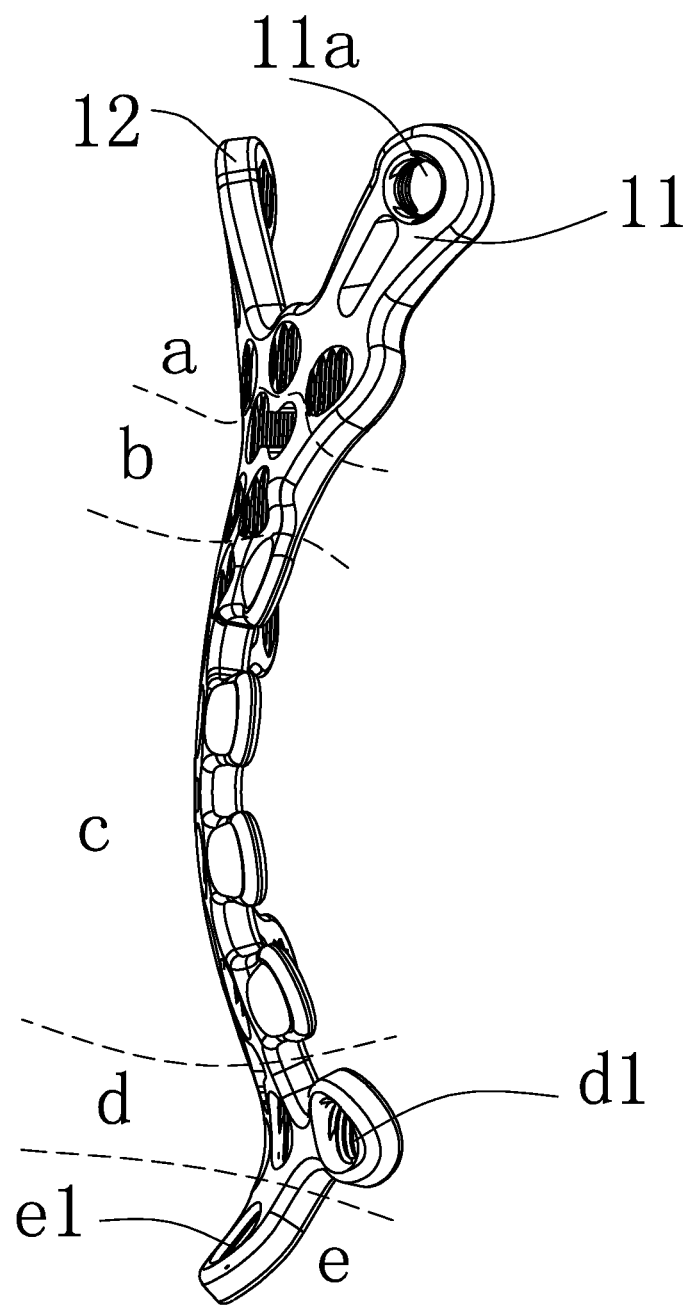
FIG. 5 is a right view of FIG. 4.
Figure 6:
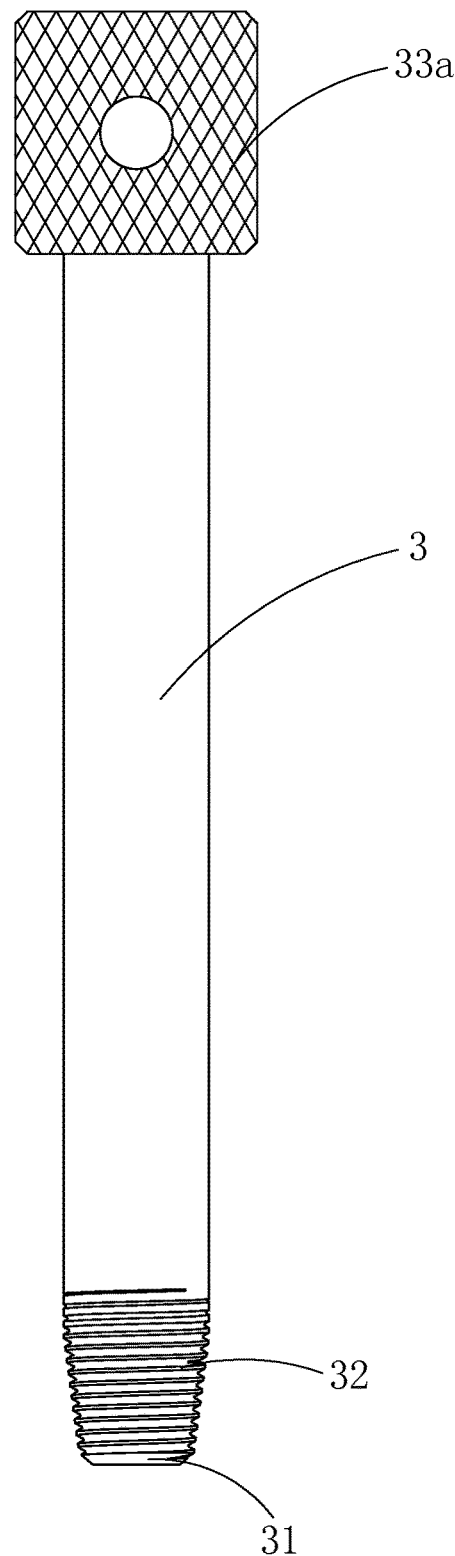
FIG. 6 is a perspective view of a guiding sleeve according to the embodiment of the present invention.
Figure 7:
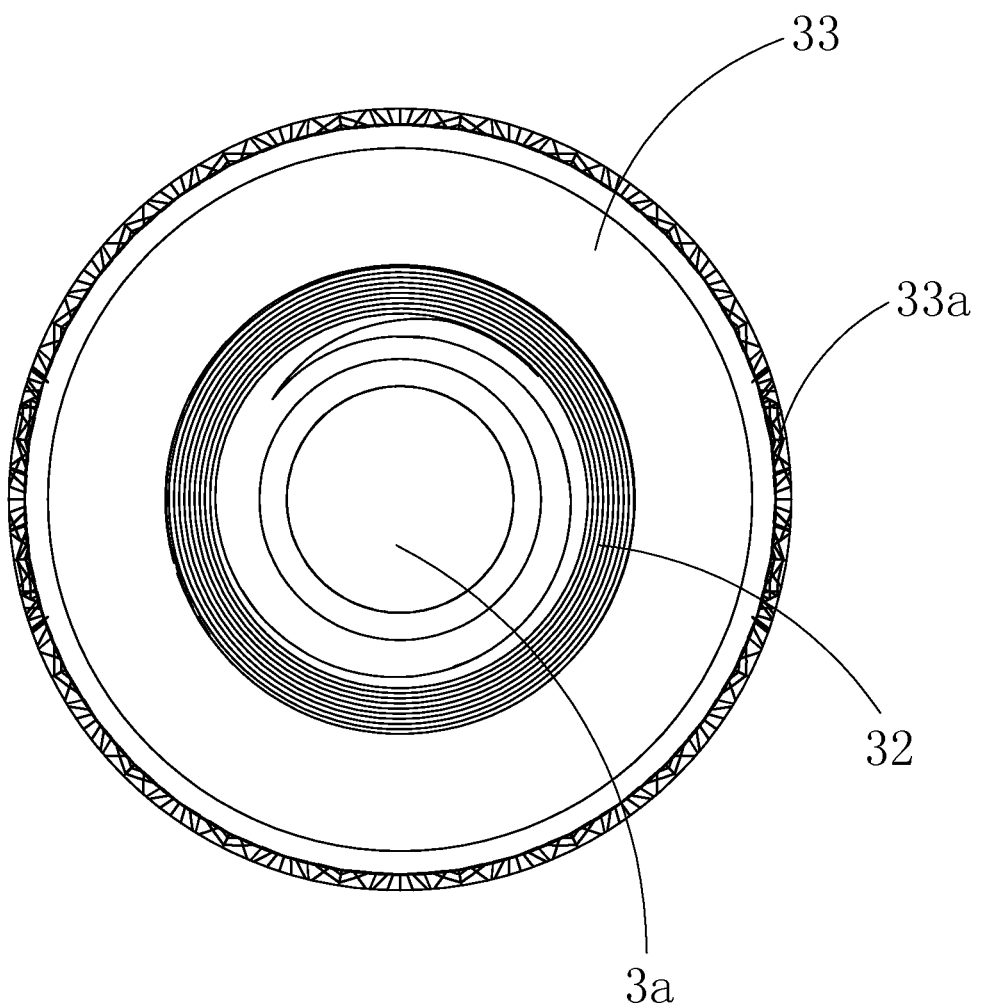
FIG. 7 is a bottom view of the guiding sleeve of FIG. 5.
Figure 8:
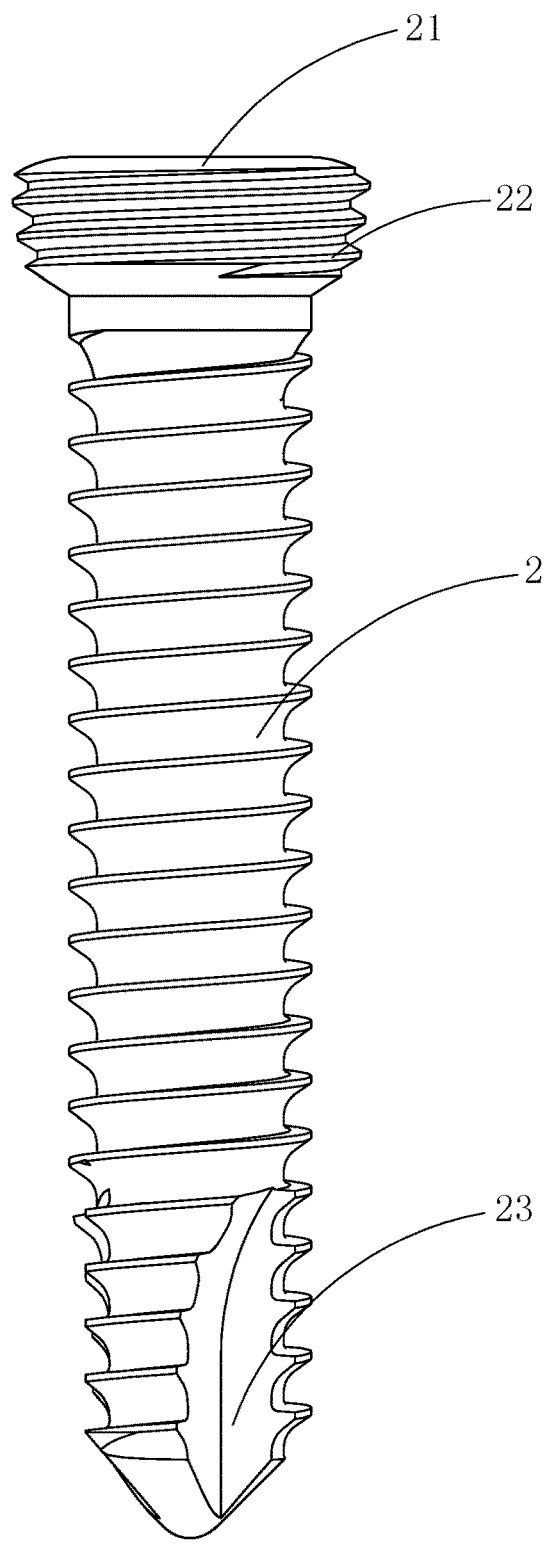
FIG. 8 is a perspective view of a locking screw according to the embodiment of the present invention.

As shown in FIG. 4, for positioning the locking holes, the right plate is defined with three longitude lines J1, J2, J3 and eleven latitude lines W1-W11; three first locking holes a1 are located on a same first latitude line W1 and respectively on the three longitude lines J1, J2, J3; at least two second locking holes b1 are provided between the first latitude line W1 and a third latitude line W3 and located in turn on a first longitude line J1 and a second longitude line J2; two, one, two, one, two, one and three third locking holes c1 are respectively located on a third latitude line W3, a fourth latitude line W4, a fifth latitude line W5, a sixth latitude line W6, a seventh latitude line W7, an eighth latitude line W8 and a ninth latitude line W9; three fourth locking holes d1 are located on a same tenth latitude line W10 and respectively on three longitude lines J1, J2, J3; the fifth locking hole e1 is located on an eleventh latitude line W11 and the second longitude line J2. A thickness of the edge of the plate is 50% to 70% of that of the central portion of the plate.

In this embodiment, one of the positioning holes c2 is located between the fifth latitude line W5 and the seventh latitude line W7, while the other positioning holes c2 is located between the ninth latitude line W9 and the tenth latitude line W10.

In this embodiment, the front projections of the region-c and the region-d are in arc bending rightward, while left projections thereof are in arc bending outward; and, the right plate has a thickness ranging from 15.0 mm to 32.0 mm and a width ranging from 5.0 mm to 18.0 mm.

Usage of the present invention is stated as follows.

Figure 9:
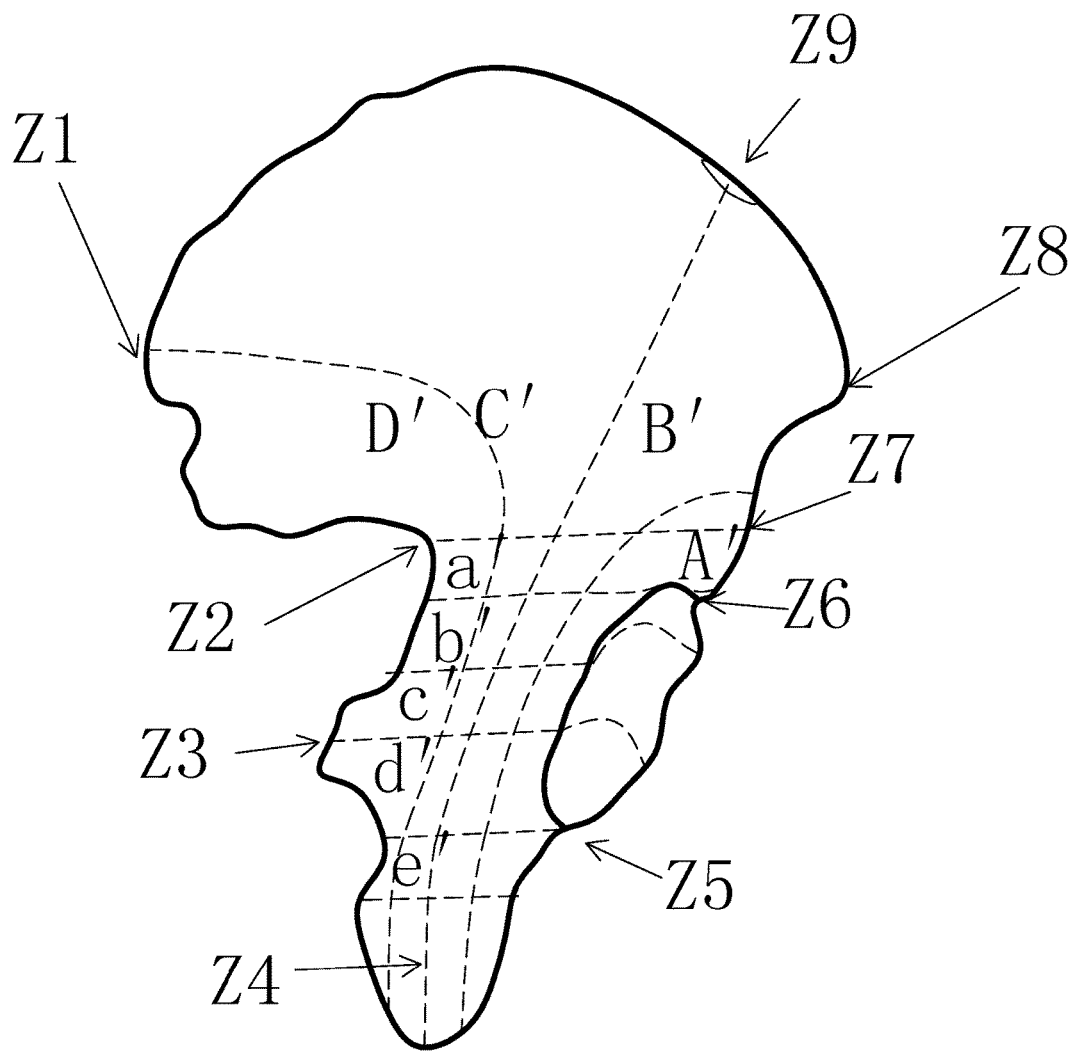
FIG. 9 is a view of the posterior of an acetabulum.

FIG. 9 shows a view of the posterior of an acetabulum and. The posterior of acetabulum is longitudinally divided by three longitudinal dashed lines in FIG. 9 into four parts, i.e., region-A', region-B', region-C' and region-D' from outside to inside in turn. A posterior bone surface of an acetabulum articular surface is uniformly divided into four parts. The posterior of acetabulum is transversely divided by six transverse dashed lines in FIG. 9 into five parts, i.e., region-a', region-b', region-c', region-d' and region-e' from top to bottom in turn.

Corresponding to the regions of the posterior of acetabulum, the right plate 1 also comprises on sideways (from outside to inside in turn) four longitudinal regions, that is region-A, region-B, region-C and region-D, and also vertically (from top to bottom in turn) comprises five transverse regions, that is region-a, region-b, region-c, region-d, and region-e.

Figure 10:
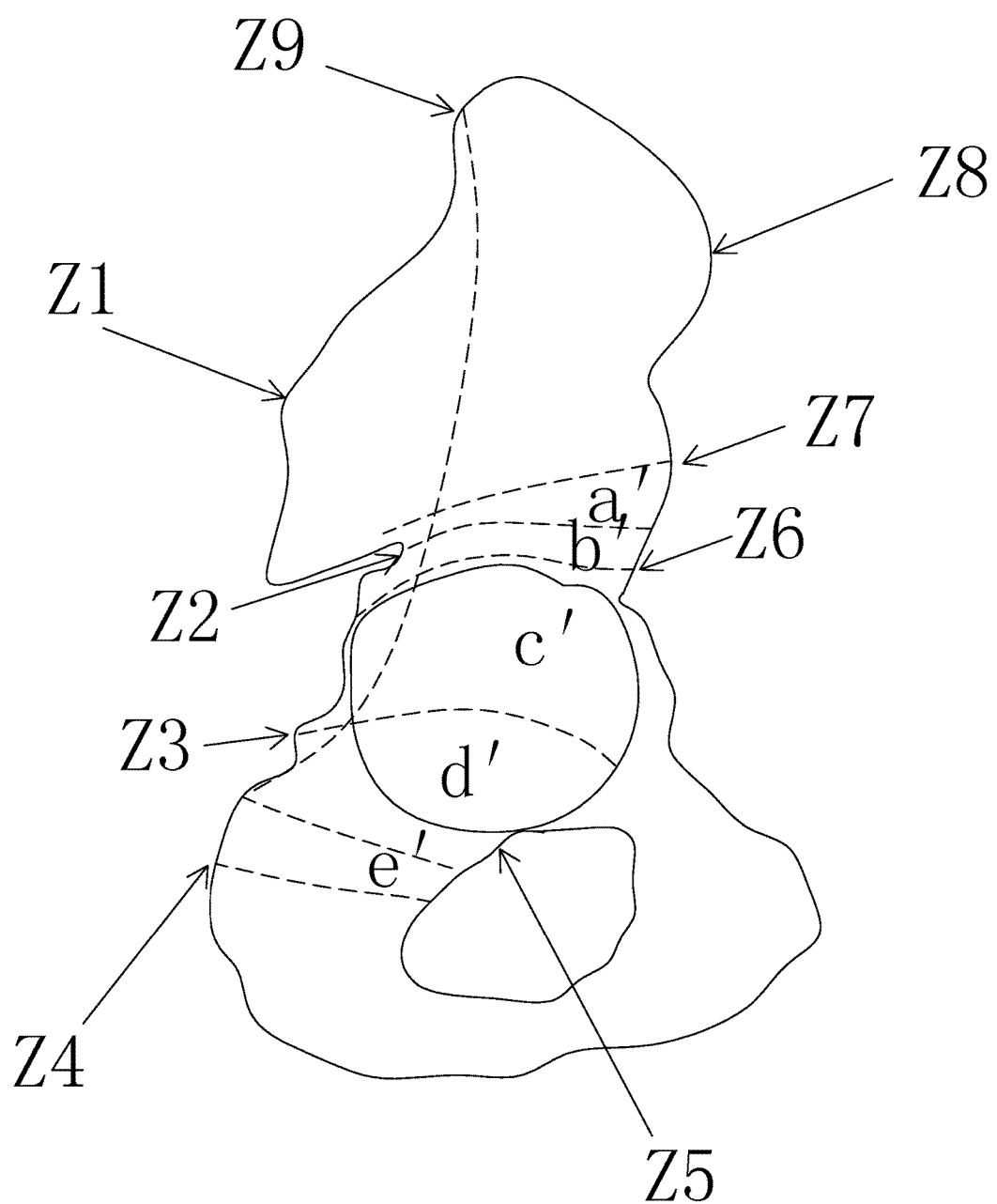
FIG. 10 is a view of the exterior of the acetabulum.

FIG. 10 shows a view of the exterior of the acetabulum. Corresponding to the transverse region division in the view of the posterior of acetabulum, the side face of acetabulum is transversely divided by six transverse dashed lines with five parts, i.e., region-a', region-b', region-c', region-d' and region-e' from top to bottom in turn. Corresponding to the five regions, the right plate 1 is also transversely defined with five transverse regions: region-a, region-b, region-c, region-d, and region-e.

Figure 11:
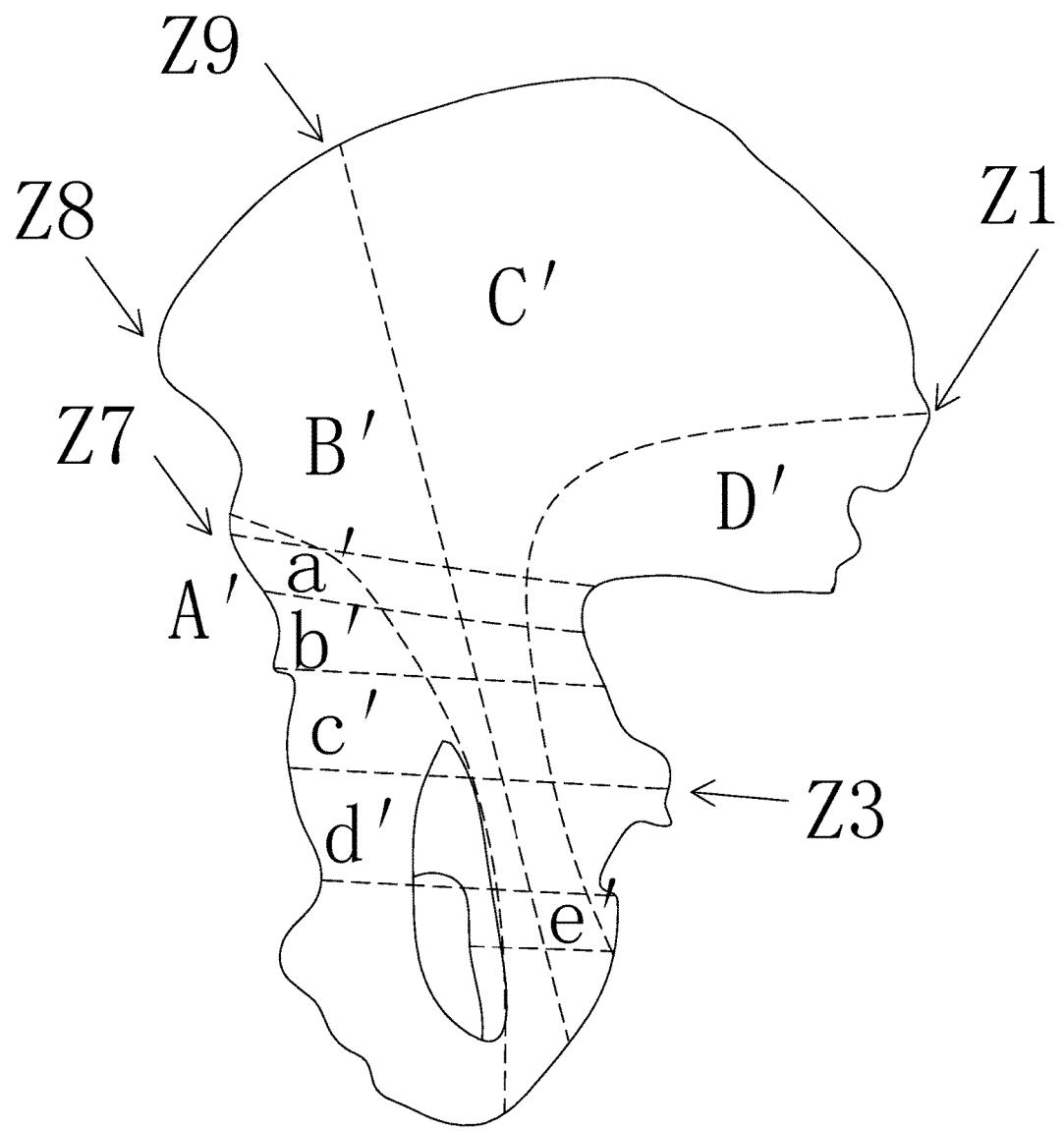
FIG. 11 is a view of the interior of the acetabulum.

FIG. 11 shows a view of the interior of the acetabulum, the longitudinal region divisions and transverse region divisions are respectively corresponding to the longitudinal and transverse region division of the posterior of acetabulum.

The characteristics of the longitudinal region divisions and transverse region divisions will be described hereinafter anatomically.

According to a transmission path of an internal force inside the pelvis and acetabulum, from the perspective of the middle of the posterior of acetabulum, from outside to inside, the posterior of acetabulum is defined with four regions in turn, i.e. region-A', region-B', region-C' and region-D', where the region-A' is an external ⅓ region of the posterior wall of acetabulum, i.e., an external ¼ region of the posterior of acetabulum, the region-B' is a middle ⅓ region of the posterior wall of acetabulum, the region-C' is an internal ⅓ region of the posterior wall of acetabulum, and the region-D' is a posterior column region of the acetabulum, i.e., an internal ¼ region of the posterior of acetabulum. The posterior of acetabulum is equally divided by a connecting line from an iliac tuberosity Z9 (iliac tubercle Z10) to a middle point of an ischial tubercle Z4.

On an external surface of the pelvis bone, a pelvic external longitudinal central axis runs from the iliac tuberosity Z9 to the middle point of the ischial tubercle Z4, called a tuberosity-ischium line and anatomically called a middle column of acetabular, where is a concentration region of longitudinal compression bone trabecula in the middle of the pelvis and acetabulum bone. The posterior of acetabulum is equally defined with an external part and an internal part by this central axis. The external and internal sides of the axis are equally defined with two regions, respectively: the external side is equally defined with region-A' and region-B' and the internal side is equally defined with region-C' and region-D'.

Region-A': a connecting line from the anterior inferior spine Z7 to an external rim of the ischial tubercle Z4, called an anterior ischial line, with the external part being an external ⅓ part of the posterior wall of acetabulum, i.e., an external ¼ region of the posterior of acetabulum.

Region-B': a part between the anterior ischial line and the tuberosity-ischium line;

Region-C': a part between a posterior ischial line and the tuberosity-ischium line; and Region-D': a connecting line from the posterior superior iliac spine Z1 to an internal rim of the ischial tubercle Z4 in a direction of bone trabecula inside the bone, called the posterior ischial line, and the internal part is an internal ¼ region of the posterior of acetabulum and anatomically called a posterior column of acetabulum.

Region-a': a region between the connecting line from the anterior inferior spine Z7 to the vertex of the greater sciatic notch Z2 and the superior acetabular rim Z6;

Region-b': a superior ⅓ part of acetabulum;

Region-c': a middle ⅓ part of acetabulum;

Region-d': an inferior ⅓ part of acetabulum; and

Region-e': a region between the inferior acetabular rim Z5 and the highest point of the ischial tubercle Z4.

The right plate 1 is designed according to a traveling direction of bone trabecula inside the pelvis and acetabulum bone. The right plate 1 includes a main body having longitudinal regions A, B, C and additional region having longitudinal region-D. An angle of torsion and a change in radian are both fit with the surface bone shape of the posterior of acetabulum and pelvis.

From the anterior, from outside to inside, the longitudinal regions A, B, C and D respectively match with the distribution direction of compression bone trabecula; from top to bottom, the five transverse regions a, b, c, d and e respectively match with the distribution direction of tension bone trabecula. The right plate 1 meets the biomechanical requirements of the pelvis and acetabulum and is additionally provided with a connecting bridge structure, so that the stress is prevented from being concentrated to break the locking screw 2 and the plate, or from being insufficient to result in failed fixation.

The region-a has three to five transverse holes, and the region-a' located at the superior part of the acetabular dome is a region 1 cm to 5 cm away from the superior rim of the acetabular dome. Those transverse holes are successively distributed in regions A'a', B'a' and C'a' to uniformly cover the bone on the acetabular dome in an umbrella form, and to secure external, middle and internal fractures of the acetabular dome and bone grafting materials. The locking screws 2 in the regions Ba and Ca may secure an anterior column of acetabulum (superior ramus of pubis) from posterior to anterior. According to the requirements of the internal fixation during the operation, common screws, locking screws 2 or cannulated locking lag screws having a diameter of 3.5 mm to 4.5 mm may be used. The length of each of the locking screws 2 may be 45 mm to 120 mm.

In the regions Aa and Da, in a direction of compression bone trabecula along the anterior ischial line of the anterior column of acetabulum and the posterior ischial line of the posterior column of acetabulum, one to two connecting holes and one groove 16 are additionally provided to enhance the fixation of the anterior column and posterior column of acetabulum. The connecting bridge structure is provided on both sides of the groove 16 to uniformly transfer the fixing force and meanwhile reduce the coverage of the plate to the bone surface, so that this protects the blood circulation at a fracture site and facilitates the fracture union. The locking screw 2 in the region Da is located above an arcuate line of pelvis, and the locking screw 2 in the region Aa is adjacent to the anterior inferior spine Z7. The remaining is the same as the main body.

The region-b has at least two transverse holes located within a superior $\frac{1}{3}$ region of the articular surface of acetabulum. The at least two holes are located in regions Bb and Cb, respectively, to secure a superior $\frac{1}{3}$ part of the acetabulum joint. The locking screws 2 in the regions have a length of 40 mm to 60 mm and may secure the anterior column and posterior column of acetabulum and the fractures in the interior of acetabulum from posterior to anterior.

For a large bone, this region may secure the fracture at the superior $\frac{1}{3}$ part of the acetabulum joint. For a medium bone or a small bone, this region may secure the fracture above the acetabular dome.

When the region-b has two rows of transverse holes, with two holes in each row, the holes are located in regions Bb/Cb, respectively, to enhance the securing of the fracture at the superior $\frac{1}{3}$ part of the acetabulum joint or above the acetabular dome.

The region-c is located in a middle $\frac{1}{3}$ region of the acetabulum joint. The main body of the right plate 1 has three longitudinal regions A, B and C, and the additional region has region-D. Region-A, region-B and region-C all have locking holes arranged longitudinally. The locking holes in the region-A are blocking holes for blocking fine bone fragments on the external rim of the posterior wall of acetabulum, and do not allow the locking screws 2 to be screwed therein. The locking holes on the region-B and region-C are designed as directional locking threads, inclined inward to evade the articular surface of acetabulum, and correspondingly secure the fracture in the middle $\frac{1}{3}$ part of the acetabulum joint, and specifically, secure the fracture in the external, middle and internal $\frac{1}{3}$ regions of the posterior wall of acetabulum in the middle $\frac{1}{3}$ part of the acetabulum joint. The locking screws 2 have a length of more than 35 mm, and can treat the fracture of quadrilateral region of the acetabulum from the posterior. A groove 16 is provided in the fourth row, and a groove 16 is provided in the seventh row, for purpose of temporarily securing a medical steel needle. Meanwhile, the grooves have a positioning function during the operation, in detail, the groove 16 in the fourth row positions the middle part of the acetabulum, while the groove 16 in the seventh row positions the inferior rim of the articular surface of acetabulum, so that it is convenient for a surgeon to judge whether the position of the plate is proper, and the locking screws 2 are prevented from intruding into the interior of the joint.

A third connecting bridge 13 and a fourth connecting bridge 14 are additionally provided in the region-D in order to strengthen the fixing of the posterior column of acetabulum, the fourth connecting hole 14a is designed for fixing the fracture of the region of ischial spine Z3. The fracture of quadrilateral region of the acetabulum can be treated from posterior to anterior. The remaining is the same as the main body.

A third connecting bridge 13 and a fourth connecting bridge 14 are additionally provided in the region-D, to enhance the posterior column of acetabulum, the fourth connecting hole 14a can secure the fracture in the ischial spine Z3 region. This hole may secure the fracture on the four interal borders of acetabulum from posterior to anterior. The remaining is the same as the main body.

The region d is in contact with the bottom of the posterior of acetabulum, and secures the inferior $\frac{1}{3}$ part of the articular surface of acetabulum, i.e., the fracture of the bottom of the posterior wall of acetabulum, specifically the external, middle and internal regions of the inferior $\frac{1}{3}$ part of the articular surface of acetabulum. In the case of the skeletal abnormalities, the locking screws 2 in this region may secure the external, middle and internal $\frac{1}{3}$ parts of ischial ramus. All the holes in this region are downward inclined, without invading into the acetabulum.

The region e is located on the longitudinal central axis (tuberosity-ischium line) of the exterior of the pelvis in the middle point from the iliac tuberosity Z9 to the ischial tubercle Z4. This axis is anatomically called a middle column of acetabulum. That is, the region c is located on the axis of longitudinal compression bone trabecula inside the pelvis and acetabulum. The region c is used for securing the ischial ramus. The direction of this region is directed to tuberculum tubercle thus to ensure an enough long screw path. The threads of the locking screws 2 may secure more bones, and the stability is thus better.

(1) The edge of the plate is circular gradient, so that the intrusion and disturbance to pelvis organs, important vascular nerves and muscular tissues are reduced, the soft tissues such as surrounding vessels are easy to be covered, and the dead space surrounding the plate is reduced.

(2) The right plate is provided with a connecting bridge structure. The bending strength and deformation curve of a uniform shape fits for the traveling direction of bone trabecula inside the pelvis and acetabulum, the biomechanical transmission path of the pelvis and acetabulum, as well as the characteristics of the surface shape of the dome, interior, anterior and posterior of the acetabulum and the structure of the internal bone trabecula. The internal stress is distributed uniformly, so that the stress at the fracture end is effectively dispersed, the risk of breaking the locking screws 2 and the plate is reduced, and it is advantageous for the plate to bear load.

(3) The mated locking screws 2 have a diameter of 2.5 mm to 4.5 mm. The commercially available common screws, locking screws 2 or cannulated locking screws may be used.

(4) According to the demand of internal fixation during the operation, all the holes are designed to allow the locking screws 2 and non-locking screws to be screwed therein.

(5) The shape of the plate and the distribution of the holes fit for the load sharing principle, the neutral principle, the principle of tension band and the principle of compression band of the internal fixation of the orthopaedic biomechanics. The stress is distributed uniformly, the failed fixation is avoided, and the locking screws 2 are effectively prevented from loosing and breaking.

(6) A hole canal in a safe direction is preset. All directionally implanted locking screws 2 evade the dispersed design of the hip joint, the obturator nerve vessel model and the superior gluteal vessel nerve model. The outlet of the locking screws 2 is located at a safe position. The inclination angle α of each locking screw 2 relative to the surface of the plate 1 can be adjust at anterior-posterior, interior-exterior, superior-inferior in range of 0° to 20° and all locking screws 2 are distributed surrounding the hip joint, so that after the locking screws 2 are screwed, a safe will be ensured.

(7) The holes of the present invention are designed with threads, and the threads of nuts may be engaged with the threads in the holes, so that the plate of the present invention is integrated with the locking screws 2, and the locking screws 2 are tightly locked with the locking holes of the plate to form a stable support structure. Consequently, better internal fixation strength is maintained, and the mechanical stability is enhanced. Under the premise of ensuring safety, all comminuted fractures in the superior-inferior, anterior-posterior and interior-exterior of the hip joint may be effectively and reliably locked and secured, so that the re-displacement of bone fragments is prevented and it is sufficient to resist against the displacement force of the fracture of the hip joint.

(8) The locking screws 2 are selectively screwed during the operation according to the requirements of securing fracture blocks, and not all holes have the locking screws 2 screwed therein.

(9) The locking screws 2 are selectively screwed during the operation according to the requirements of securing fracture blocks. For the fine bone fragments into which it is difficult to allow the locking screws 2 to be screwed, the plate may block the fine bone fragments, so that the better restoration of the bone fragments is maintained, and the loss of bone is avoided. Meanwhile, the holes provide a passageway for vessel implantation.

(10) After screwed, the locking screws 2 may secure fracture blocks and bone grafting materials on the posterior wall of the posterior column of the acetabulum, the anterior wall of the anterior column of acetabulum, acetabular dome and the interior of acetabulum, so that the normal mating and alignment between the articular surface and the femoral head is maintained, and the normal stable state of the hip joint is kept.

(11) During the hip joint replacement, in the cases where the bone defects on the dome and interior of the acetabulum require bone grafting, the present invention may ensure the stability of a bone graft.

(12) A guiding sleeve 3 for directional drilling is provided, to ensure that the screw path is safe and will not intrude into the interior of a joint.

(13) The plate of the present invention allows for moderate torsion within a three-dimensional space so as to realize better fit with a bone model.

(14) The plate of the present invention may be made of medical stainless steel, medical titanium alloy, or medical absorbable high-strength material.

(15) Data, such as a ratio of change in the thickness, radian and angle of torsion of the plate, and in the diameter, threads and pitch of nuts of the locking screws 2, fits for the requirements of the golden section principle.

(16) All the holes and grooves 16 are used as vessel placement passageways.

Although the preferred embodiments of the present invention have been described, various variations or modifications may be made by a person of ordinary skilled in the art without departing from the scope of the present invention.

The invention claimed is:

1. A universal self-locking anatomical plate for posterior of acetabulum and pelvis, comprising a right plate (1), a plurality of screws (2) and a guiding sleeve (3) for guiding drilling of the screws (2),
wherein
the right plate has a central axis, a longitudinal section, an edge, and a central portion,
the longitudinal section along the central axis of the right plate (1) has a smooth arc surface, and
the right plate (1) vertically comprises a first locking block (a), a second locking block (b), a third locking block (c), a fourth locking block (d) and a fifth locking block (e), which are all in arc;
the right plate (1) comprises, on sideways, a region-A, a region-B, a region-C and a region-D;
the first locking block (a) is provided thereon with three first locking holes (a1) for receiving the screws (2), the second locking block (b) is provided thereon with at least two second locking holes (b1), the third locking block (c) is provided thereon with two positioning holes (c2) and twelve third locking holes (c1), the fourth locking block (d) is provided thereon with three fourth locking holes (d1), and the fifth locking block (e) is provided thereon with one fifth locking hole (e1); and an angle (α) between each of the first locking holes (a1), the second locking holes (b1), the third locking holes (c1), the fourth locking holes (d1), and the fifth locking hole (e1) and the surface of the right plate (1) is in range of 0°-20°; and
each of the first locking holes (a1), the second locking holes (b1), the third locking holes (c1), the fourth locking holes (d1), and the fifth locking hole (e1) has an internal thread;
a first connecting bridge (11) and a second connecting bridge (12) are extended outward from the first locking block (a), the first connecting bridge (11) defines a first connecting hole (11a), the second connecting bridge (12) defines a second connecting hole (12a);
a third connecting bridge (13) and a fourth connecting bridge (14) are extended laterally away from the third locking block (c), the third connecting bridge (13) defines a third connecting hole (13a), the fourth connecting bridge (14) defines a fourth connecting hole (14a), the third connecting bridge and the fourth connecting bridge defining a U-shape;
the second connecting bridge (12), the third connecting bridge (13) and the fourth connecting bridge (14) each defines a groove (16), and each groove (16) is respectively closer to the central axis of the right plate (1) relative to the first connecting hole (11a), the second connecting hole (12a), the third connecting hole (13a) and the fourth connecting hole (14a); and
two compensation holes (c3) are respectively provided at a joint between the third connecting bridge (13) and a region-c, and a joint between the fourth connecting bridge (14) and the region-c, each compensation hole (c3) is in communication with an adjacent groove (16), each compensation hole has a first diameter that is larger than a width of the groove, and the grooves have a width that is smaller than a diameter of each of compensation holes.

2. The plate according to claim 1, wherein each groove (16) is 3-5 mm in length and 2.5 mm in width.

3. The plate according to claim 1, wherein a first annular gap (15) is provided between the third locking holes (c1) on a rightmost edge of the region-c, and a second annular gap

(15) is also provided between the fourth locking hole (d1) on a rightmost edge of a region-d and adjacent third locking hole (c1).

4. The plate according to claim 1, wherein for positioning the locking holes, the right plate is defined with three longitude lines (J1,J2,J3) and eleven latitude lines (W1-W11);

three first locking holes (a1) are located on a same first latitude line (W1) and respectively on the three longitude lines (J1, J2, J3); at least two second locking holes (b1) are provided between the first latitude line (W1) and a third latitude line (W3) and located in turn on a first longitude line (J1) and a second longitude line (J2);

two, one, two, one, two, one and three third locking holes (c1) are respectively located on a third latitude line (W3), a fourth latitude line (W4), a fifth latitude line (W5), a sixth latitude line (W6), a seventh latitude line (W7), an eighth latitude line (W8) and a ninth latitude line (W9);

three fourth locking holes (d1) are located on a same tenth latitude line (W10) and respectively on three longitude lines (J1, J2, J3); the fifth locking hole (e1) is located on an eleventh latitude line (W11) and the second longitude line (J2);

and, a thickness of the edge of the plate is 50% to 70% of that of the central portion of the plate.

5. The plate according to claim 4, wherein one of the positioning holes (c2) is located between the fifth latitude line (W5) and the seventh latitude line (W7), while the other positioning hole (c2) is located between the ninth latitude line (W9) and the tenth latitude line (W10); and front projections of the region-c and a region-d are in arc bending rightward, while left projections thereof are in arc bending outward; and, the right plate has a thickness ranging from 15.0 mm to 32.0 mm and a width ranging from 5.0 mm to 18.0 mm.

6. The plate according to claim 1, wherein a region-a can fix outer, middle and inner regions of dome of the acetabulum and simultaneously can fix an anterior column of the acetabulum from posterior to anterior;

the second connecting hole (12a) is designed for strengthening fixing of a posterior column of the acetabulum, and the first connecting hole (11a) is designed for strengthening fixing of the anterior column of the acetabulum;

a region-b can fix outer, middle and inner regions of an upper ⅓ part of a joint of the acetabulum; the screws are screwed from the posterior into the anterior in order to fix the anterior and posterior columns of the acetabulum and a medial side of the acetabulum;

the region-c can fix the outer, the middle and the inner regions of a middle ⅓ part of the joint of the acetabulum, and the screws are screwed from the posterior into the anterior part in order to fix the quadrilateral region of the acetabulum; the two grooves (16) on the region-c can respectively position a middle portion and an inferior margin of an articular surface of the acetabulum; the third connecting hole (13a) and the fourth connecting hole (14a) are designed for securing the posterior column of the acetabulum and an ischial spine (Z3);

a region-d can fix the outer, the middle and the inner regions of a ⅓ part lower the articular surface of the acetabulum; and the region-e can fix a ramus of ischium;

while, the region-A, region-B, region-C and region-D, these four longitudinal regions, from outside to inside in turn, respectively fix one longitudinal ¼ part of the posterior of the acetabulum.

7. The plate according to claim 6, wherein the screws used in the region-a has a length between 30 mm to 120 mm, and the screws used in the region-b has a length between 30 mm to 60 mm.

8. The plate according to claim 6, wherein the screws (2) can be common screws, locking screws (2), or cannulated lag screws.

* * * * *